United States Patent [19]

Caldwell et al.

[11] Patent Number: 4,746,669

[45] Date of Patent: May 24, 1988

[54] SUBSTITUTED THIAZOLES AS IMMUNOREGULANTS

[75] Inventors: Charles G. Caldwell, Scotch Plains; Ihor Kopka, Newark; Milton L. Hammond, Sommerville; Robert A. Zambias, Springfield, all of N.J.

[73] Assignee: Merck & Co., Inc., Rahway, N.J.

[21] Appl. No.: 30,313

[22] Filed: Mar. 26, 1987

Related U.S. Application Data

[63] Continuation of Ser. No. 812,471, Dec. 23, 1985, abandoned.

[51] Int. Cl.⁴ ................... A61K 31/38; C07D 409/04; C07D 409/06; C07D 217/04; C07D 277/22

[52] U.S. Cl. ..................... 514/342; 544/298; 544/300; 544/405; 544/180; 544/215; 544/297; 514/252; 514/256; 514/307; 514/314; 514/333; 514/338; 514/339; 514/337; 514/362; 514/363; 514/367; 514/365; 546/280; 546/141; 546/142; 546/143; 546/144; 546/145; 546/148; 546/153; 546/155; 546/157; 546/159; 546/256; 548/202; 548/203; 548/204; 548/205; 548/186; 548/187; 548/184; 548/181; 548/134; 548/135; 548/136; 548/138

[58] Field of Search .................. 546/280; 514/342

[56] References Cited

U.S. PATENT DOCUMENTS

| | | | |
|---|---|---|---|
| 3,821,384 | 6/1974 | Ariyan et al. | 546/280 |
| 4,260,765 | 4/1981 | Harrison et al. | 546/280 |
| 4,363,813 | 12/1982 | Kawasaki et al. | 546/280 |
| 4,385,059 | 5/1983 | Franklin | 546/280 |

OTHER PUBLICATIONS

Goodman et al., The Pharmacological Basis of Therapeutics, p. 28.

*Primary Examiner*—Mary Lee
*Assistant Examiner*—J. Richter
*Attorney, Agent, or Firm*—Theresa Y. Cheng; Micahel C. Sudol

[57] ABSTRACT

Thiazole derivatives have been made, for example, by reacting a 2-aryl-2,2-dialkoxyethylamine with an appropriately substituted aryl acetyl halide followed by treating the resulting amide with diphosphoryl pentasulfide. The thiazole derivatives are found to be effective immunoregulants.

9 Claims, No Drawings

SUBSTITUTED THIAZOLES AS IMMUNOREGULANTS

This is a continuation of application Ser. No. 812,471, filed on Dec. 23, 1985, now abandoned.

BACKGROUND OF THE INVENTION

Immunoregulatory abnormalities have been shown to exist in a wide variety of "autoimmune" and chronic inflammatory diseases, including systemic lupus erythematosis, rheumatoid arthritis, type 1 diabetes mellitus, inflammatory bowel disease, multiple sclerosis and contact sensitivity. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, in transplantation, the host lymphocytes recognize the foreign tissue antigens and begin to produce antibodies which lead to the rejection of the transplanted organ.

The end result of an autoimmune or a rejection process is tissue destruction caused by inflammatory cells and the mediators they release. Antiinflamatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Accordingly, an object of the present invention is to provide various thiazole derivatives as immunoregulants which will (1) restore the normal balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide pharmaceutical compositions for administering the active compounds as immunoregulants.

Still a further object of this invention is to provide a method of controlling transplant rejection, autoimmune and chronic inflammatory diseases by administering a sufficient amount of one or more of the active compound in a mammalian species in need of such treatment.

Finally, it is the object of this invention to provide chemical processes for the preparation of the active compounds.

DETAILED DESCRIPTION OF THE INVENTION

A. Scope of the Invention

This invention relates to immunoregulants of formula:

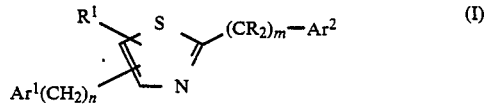

or a pharmaceutical salt thereof wherein
$Ar^1$ and $Ar^2$ independently are
(a) phenyl of formula

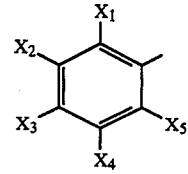

wherein $X_1$, $X_2$, $X_3$, $X_4$ and $X_5$ independently are
(1) hydrogen;
(2) halo especially fluoro, chloro or bromo;
(3) loweralkoxy especially $C_{1-6}$ alkoxy, e.g., methoxy, ethoxy, isopropoxy, t-butoxy or cyclohexyloxy, or —$OCH_2O$—;
(4) loweralkylthio especially $C_{1-6}$ alkylthio, or $C_{1-6}$ haloalkylthio e.g., methylthio, ethylthio, trifluoromethylthio or cyclohexylthio;
(5) loweralkylsulfinyl especially $C_{1-6}$ alkyl sulfinyl, e.g., methyl sulfinyl, i-propyl sulfinyl, and cyclopentyl sulfinyl;
(6) loweralkylsulfonyl especially $C_{1-6}$ alkylsulfonyl such as methylsulfonyl, ethylsulfonyl and n-butylsulfonyl;
(7) unsubstituted or substituted phenyl loweralkoxy such as benzyloxy;
(8) loweralkyl especially $C_{1-6}$ alkyl such as methyl, ethyl, propyl, t-butyl, pentyl, benzyl, cyclopropyl, cyclopentyl or cyclohexyl;
(9) loweralkenyl especially $C_{2-6}$ alkenyl, for example, vinyl, allyl, and buten-2-yl;
(10) loweralkanoyl especially $C_{1-6}$ alkanoyl such as formyl, acetyl or i-propanoyl;
(11) haloloweralkyl especially $C_{1-6}$ haloalkyl such as trifluoromethyl;
(12) —$COOR_a$ wherein $R_a$ is H or $C_{1-6}$ alkyl;
(13) aryl especially phenyl or substituted phenyl, e.g., 4-methoxyphenyl,2,4-difluorophenyl or 3-chlorophenyl; or
(14) aryloxy especially phenoxy or aryl-S- especially phenyl-S-;
(15) cyano;
(16) hydroxyloweralkyl especially hydroxy $C_{1-3}$ alkyl such as —$CH_2OH$;
(17) haloloweralkanoyl especially halo$C_{1-6}$ alkanoyl eq. $CF_3CO$;
(18) loweralkanoyloxy especially acetyloxy;
(19) unsubstituted or substituted heteroaryl, for example:
(a) thienyl;
(b) benzothienyl;
(c) furyl;
(d) benzofuryl;
(e) pyrryl;
(f) indolyl;
(g) thiazolyl;
(h) benzothiazolyl;
(i) thiadiazolyl;

(j) benzothiadiazolyl;
(k) quinolyl;
(l) isoquinolyl;
(m) pyridyl;
(n) pyrazinyl;
(o) tetrazolyl;
(p) triazolyl;
(q) imidazolyl; or
(r) pyrimidinyl;
the heteroaryl above can be substituted with one or more functional groups as previously represented by $X_1$, $X_2$, $X_3$ or $X_4$ and particularly, $C_{1-6}$ alkyl, $C_{1-6}$ alkanoyl, $C_{1-6}$ Haloalkyl, halo, cyano, or hydroxy $C_{1-3}$ alkyl;
(20) —$NR_aCOR_b$ wherein $R_a$ and $R_b$ independently are H or $C_{1-6}$ alkyl;
(21) —$NO_2$;
(22) —$NR_aR_b$;
(23) —$OR_a$;
(24) —$CONR_aR_b$
(25) —$COR_a$;
(26) —$NR_aCONR_bR_b$;
(27) —$NR_aCOR_b$;
(28) —$OCOR_a$;
(29) —$SCOR_a$;
(30) —$OCH_2O$—; or
(31) heterocyclic, e.g., piperidinyl;
(b) heteroaryl as previously defined; with the proviso that $Ar^1$ and $Ar^2$ cannot be simultaneously 4-(4-pyridyl) and phenyl of formula

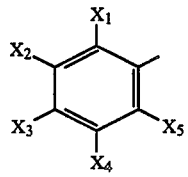

(c) heterocyclic, e.g., piperidinyl;
R can be connected to the aralkyl carbon with a single or a double bond: for double bond-connection, R can only be =O, =S, =$NR_a$, or =CH—$R_c$ wherein $R_c$ is $R_a$, —$COOR_a$, —$CONR_aR_b$, CN, $OR_a$, or halo; for single-bond connection, there can be one or two sets of R and each R independently is $R_c$;
$R^1$ is $R_a$, halo or haloloweralkyl; and
m and n independently are 0 to 4.
In a preferred embodiment of this invention $Ar^1$ and $Ar^2$ independently are
(a) phenyl of formula

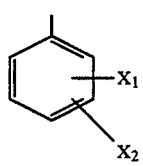

(b) 5-(4-pyridyl) of formula

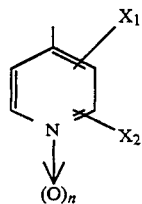

wherein
X, and $X_2$ independently are
(1) hydrogen;
(2) halo;
(3) —$OR_a$;
(4) $C_{1-6}$ alkylthio;
(5) $C_{1-6}$ alkyl;
(6) —$CF_3$;
(7) phenyl;
(8) —CN;
(9) —$NR_aCOR_b$;
(10) —$NO_2$;
(11) —$NR_aR_b$;
(12) —$CONR_aR_b$
(13) —$NR_aCONR_bR_a$; or
(14) heteroaryl or substituted heteroaryl especially pyridyl thienyl, or thiazolyl;
n is 0 or 1;
(c) piperidinyl;
R is hydrogen; and
$R^1$ is $R_a$.
In a more preferred embodiment of this invention, the compounds of the present invention are of formula:

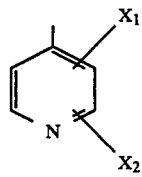

wherein:
$Ar^1$ is 5-(4-pyridyl) of formula

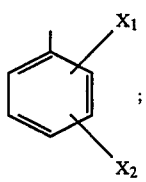

$Ar^2$ is phenyl of formula or pyridyl of formula

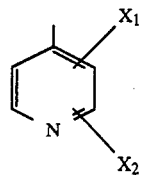

$X_1$ and $X_2$ independently are
(1) hydrogen;
(2) $C_{1-6}$ alkyl;
(3) $-NR_aR_b$; or
(4) halogen;
R is hydrogen or F; and
$R^1$ is H;

B. Preparation of the compounds within the scope of the present invention

The compounds of formula (I) are prepared from known starting materials according to the following synthetic schemes:

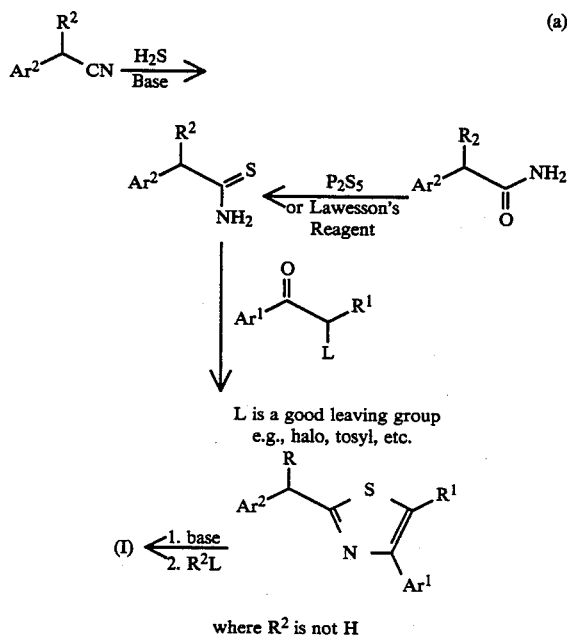

(a)

L is a good leaving group e.g., halo, tosyl, etc.

where $R^2$ is not H

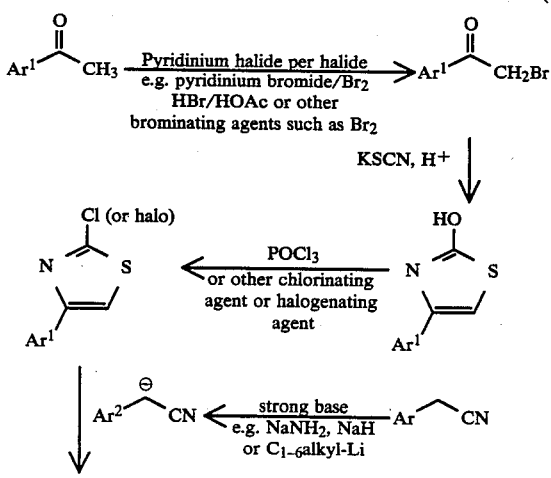

(b)

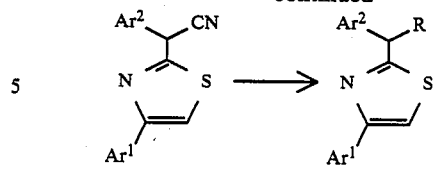

wherein R is $-COOR_a$ or $-CONR_aR_b$ and $R_a$ and $R_b$ are independently H or $C_{1-6}$alkyl.

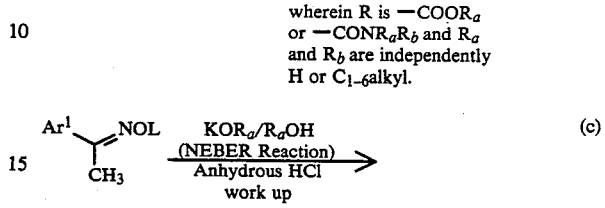

(c)

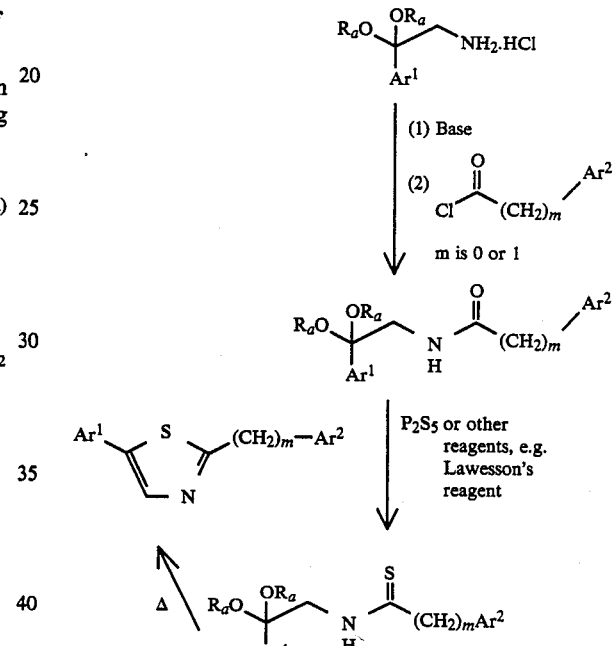

C. Utility of the compounds within the scope of the invention

This invention also relates to a method of treatment for patients suffering from autoimmune diseases. More specifically, it relates to a method of treatment involving the administration of a compound of formula (I) as the active constituent.

For the treatment of autoimmune diseases a compound of formula (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of ethylene oxide with a long chain aliphatic alcohol, for example, heptadecaethyleneoxycetanol,
 (d) a condensation product of ethylene oxide with a partial ester derived from a fatty acid and a hexitol such as polyoxyethylene sorbitol monooleate, or
 (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl aclohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

Dosage levels of the order from about 0.5 mg to about 100 mg per kilogram of body weight per day are useful in the treatment of the above-indicated conditions (from about 25 mg to about 5 gms. per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate but do not limit the present invention.

EXAMPLE 1

2-Benzyl-5-(4-pyridyl)thiazole

Step A: Preparation of α-amino-4-acetylpyridine diethylketal dihydrochloride

To a solution of potassium ethoxide (15.0 g, 0.267 mol) in absolute ethanol (225 ml) was added a solution of 4-acetylpyridine oxime toylate (64.7 g, 0.214 mol) in absolute ethanol (400 ml) over one minute. The potassium tosylate began to form immediately and the mixture was allowed to stir for 15 minutes with ice cooling followed by 2 hours at ambient temperature. The mixture was filtered and the filter cake washed with ether (500 ml). The combined filtrate and washings were diluted with an additional portion of ether (300 ml) and refiltered. The filtrate was further diluted with ether (250 ml) then anhydrous hydrochloric acid was slowly bubbled into the filtrate until a burgundy suspension was obtained that did not change. The product was filtered off as the dihydrochloride and washed with ether. After air drying α-amino-4-acetylpyridine diethylketal dihydrochloride was obtained (44.0 g, 73%). m.p. 219°-221° dec.

Step B: Preparation of α-amino-4-acetylpyridine diethyl ketal phenylacetamide

A solution of α-amino-4-acetylpyridine diethylketal dihydrochloride (10.04 g, 0.035 mol) in water (100 ml) was basified with 2.5N sodium hydroxide (28 ml). The resulting solution was extracted with chloroform (5×50 ml) and the combined extracts were dried over sodium sulfate and concentrated to afford α-amino-4-acetylpyridine diethylketal (7.00 g). The free base was taken up in ether (75 ml) and to the resulting solution was added sequentially triethylamine (4.6 ml) and a solution of phenacetylchloride (4.3 ml) in ether (15 ml) dropwise. The mixture was allowed to stir at ambient temperature for 1.5 hours, then filtered and the filtrate washed with ether. The filtrate and washings were concentrated to a yellow solid which was triturated with 40% ether in hexane to afford α-amino-4-acetylpyridine diethylketal phenylacetamide (8.90 g, 83%). Recrystallization from hexane/ether afforded pure material. m.p. 87°-89°.

Step C: Preparation of 2-benzyl-5-(4-pyridyl)thiazole

An intimate mixture of α-amino-4-acetylpyridine diethylketal phenylacetamide (2.48 g, 0.0076 mol) and phosphorous pentasulfide (3.36 g, 0.0076 mol) was carefully heated with an oil bath under nitrogen. At a bath temperature of 115° a vigorous reaction took place. The resulting mixture was maintained at 110°-120° for ten minutes, allowed to cool, and then 5% sodium bicarbonate solution was carefully added. The solid mass was broken up mechanically and the mixture warmed and stirred for 15 minutes. After cooling the mixture was diluted with chloroform (150 ml), filtered through celite and the layers separated. The aqueous fraction was reextracted with chloroform (3×50 ml) and the combined extracts were washed sequentially with 5% sodium bicarbonate (100 ml), and saturated sodium chloride (100 ml), dried over sodium sulfate and concentrated to afford a crude product. Chromatography over silica gel (98.2 chloroform/methanol as eluant) afforded 2-benzyl-5-(4-pyridyl)thiazole (480 mg, 25%) as an oil which crystallized upon standing in the cold. Recrystallization of a sample from hexane afforded analytically pure material. m.p. 46°-47°.

EXAMPLE 2

2-Benzyl-4-(4'-pyrimidinyl)thiazole

A solution of 4-acetylpyrimidine (61.4 mg, 0.50 mmol) in 1.5 ml of acetic acid was stirred at 25° C. as 0.15 ml (0.19 g, 0.73 mmol) of 31% hydrobromic acid in acetic acid was added. Pyridinium bromide perbromide (180 mg, 0.56 mmol) was added, rapidly dissolving before a yellow precipitate formed. The reaction gradually became homogeneous over a period of 10 minutes, and then a pale yellow precipitate formed. After an additional 20 minutes, ether (5 ml) was added. The supernatant was removed by pipet, and the precipitate was washed with 4×1.5 ml of ether before being dried briefly under vacuum. The pale yellow crystals (137 mg) were dissolved in 4.0 ml of ethanol and benzylthioamide (85 mg, 0.56 mmol) was added. The solution was heated to reflux for 0.5 hour, cooled to 25° C. and partitioned between 25 ml of ether and 25 ml of 2.5N aqueous sodium hydroxide. The aqueous layer was extracted with 25 ml of ether, and the organic extracts were combined, dried (sodium sulfate), decanted, and evaporated. The residue was purified by column chromatography on silica gel (7 g) eluting with ethyl acetate (15% increasing to 20%) in dichloromethane, yielding 2-benzyl-4-(4'-pyrimidinyl)thiazole (108 mg, 85% yield) as almost colorless crystals. Recrystallization from hexane yielded colorless needles, m.p. 98°-99° C.

EXAMPLE 3

2-Benzyl-4-(1'-methyl-5'-imidazolyl)thiazole hydrochloride

A solution of 5-acetyl-1-methylimidazole (100 mg, 0.81 mmol) in 2.4 ml of acetic acid was stirred at 25° C. as 0.24 ml (0.30 g, 1.2 mmol) of 31% hydrobromic acid in acetic acid was added. Pyridinium bromide perbromide (0.29 g, 0.91 mmol) was added, giving an orange solution from which a yellow precipitate formed after 30 minutes. After 2.5 hours, ether (5 ml) was added. The supernatant was removed by pipet, and the precipitate was dried under a stream of nitrogen. Ethanol (6 ml) and benzylthioamide (137 mg, 0.91 mmol) were added, and the mixture was heated to reflux for 45 minutes. The reaction was cooled to 25° C., poured into 25 ml of ether, and washed with 50 ml of 1.25N aqueous sodium hydroxide. The aqueous layer was extracted with 2×25 ml of ether, and the organic extracts were combined, dried (sodium sulfate), filtered, and evaporated. The residue was purified by column chromatography on silica gel (5 g), eluted with 8% isopropanol in 4:1 dichloromethane/ethyl acetate, yielding 2-benzyl-4-(1'- methyl-5'-imidazolyl)thiazole (159 mg, 77% yield) as an almost colorless oil.

The free base (159 mg, 0.62 mmol) was dissolved in 10 ml of methanol and treated with 0.32 ml (0.64 mmol) of 2.0N aqueous hydrochloric acid. Evaporation of the solution yielded 183 mg of pale yellow crystals. Recrystallization from 2:1 ethyl acetate/ethanol gave 2-benzyl-4-(1'-methyl-5'-imidazolyl)thiazole hydrochloride (111 mg, 61% recovery) as colorless plates, m.p. 191°–194° C.

EXAMPLE 4

2-Benzyl-4-(1'-benzoyl-4'-piperidinyl)thiazole

Thionyl chloride (2.0 ml, 3.3 g, 27 mmol) was added to 1-benzoyl-4-piperidinecarboxylic acid (0.31 g, 1.33 mmol) at 25° C. After stirring for 48 hours, the solution was warmed to 30° C. and concentrated under a stream of nitrogen. The 1-benzoyl-4-piperidinecarbonyl chloride, sufficiently pure for subsequent reactions, was obtained as a colorless oil which crystallized during storage at 0° C.

A distilled solution of diazomethane was prepared by the slow addition of N-methyl-N-nitroso-p-toluenesulfonamide (0.88 g, 4.11 mmol) in ether (10 ml) to a 60°–65° C. solution of 87% potassium hydroxide (1.00 g, 15.5 mmol) in ethanol (2 ml) and water (1.6 ml). The receiving flask was cooled in an ice bath during the distillation. The ice bath was then removed, the flask was fitted with an addition funnel, and a solution of the crude 1-benzoyl-4-piperidinecarbonyl chloride in 3 ml of 1:1 ether/dichloromethane was added over a period of 5–10 minutes. The solution was allowed to warm to 25° C. and stirred for 1.5 hours. The reaction was then cooled in an ice bath and dry hydrogen bromide gas was bubbled through the solution for 5–10 minutes. Water (10 ml) was added, followed by ether (10 ml). The aqueous layer was extracted with 10 ml of ether. The combined organic extracts were washed with 10 ml of saturated aqueous sodium bicarbonate and 10 ml of saturated aqueous sodium chloride. The solution was dried (magnesium sulfate), filtered, and evaporated to give crude 1-benzoyl-4-(bromoacetyl)piperidine as 347 mg of pale yellow oil.

The crude bromoketone was dissolved in 5 ml of ethanol, benzylthioamide (185 mg, 1.22 mmol) was added, and the reaction was heated to reflux for 2 hours. Triethylamine (1.5 ml) was added to the cooled reaction, and the mixture was then evaporated. The residue was purified by column chromatography on silica gel (15 g), eluted with 3:2 ethyl acetate/hexane, yielding 2-benzyl-4-(1'-benzoyl-4'-piperidinyl)thiazole (267 mg, 55% yield) as an oil which crystallized during storage at 0° C. Recrystallization from 1.5 ml of toluene provided fine white crystals (174 mg), m.p. 126°–128° C.

EXAMPLE 5

2-Benzyl-4-(4'-piperidinyl)thiazole hydrochloride

A solution of 87% potassium hydroxide (2.04 g, 32 mmol) in 9.0 ml of water and 1.0 ml of methanol was added to 2-benzyl-4-(1'-benzoyl-4'-piperidinyl)thiazole (222 mg, 0.61 mmol) and the reaction was warmed to reflux for 24 hours. The reaction was then cooled to 25° C., poured into 30 ml of saturated aqueous sodium chloride, and extracted with 3/×30 ml of ethyl acetate. The combined organic extracts were washed with 30 ml of saturated aqueous sodium chloride, dried (sodium sulfate), decanted, and evaporated. The residue was purified by column chromatography on silica gel (7 g), eluted with 5% triethylamine in 3:1 dichloromethane/isopropanol to give 2-benzyl-4-(4'-piperidinyl)-thiazole (154 mg, 97% as a solid which resisted attempts at recrystallization. This material was combined with 148 mg of 2-benzyl-4-(4'-piperidinyl)thiazole obtained by the same method, treated with 1.5 ml of boiling acetonitrile, cooled, filtered to remove a small amount of insoluble material, and evaporated. The residue was dissolved in 5 ml of ethanol, 0.5 ml of 2.0N aqueous hydrochloric acid was added, and the solution was evaporated. The residue was dissolved in 2 ml of boiling acetonitrile with the aid of a few drops of ethanol. Cooling to 0° C. yielded 2-benzyl-4-(4'-piperidinyl)thiazole hydrochloride (162 mg) as pale tan crystals, m.p. 187°–188° C. The mother liquor was evaporated and recrystallized from acetonitrile/ethanol to give an additional 90 mg of pale tan crystals, m.p. 185°–187° C.

EXAMPLE 6

2-(2-Pyrrylmethyl)-4-(4-pyridyl)thiazole

Step A: Preparation of 2-(N,N-dimethylaminomethyl)pyrrole

A solution of 42.5 g (0.52 mole) of dimethylamine hydrochloride in 41 g of 38% formaldehyde (0.525 mole) was added slowly to 36.5 g (0.50 mole) of pyrrole in a 3-neck round-bottomed flask, fitted with a mechanical stirrer, reflux condenser and a dropping funnel at such a rate that the temperature did not exceed 60° C. About 30 to 60 minutes was needed to complete the addition. Stirring was continued for 1.5 hours after the addition was completed. The mixture was allowed to stand overnight. Then it was poured into 100 ml of 25% sodium hydroxide and extracted with 3/×100 ml of ether. The pooled organic layer was washed with 2/×30 ml of brine and dried over anhydrous MgSO$_4$. The solution was filtered and the ether removed under reduced pressure. 50.4 g (69%) of 2-(N,N-dimethylaminomethyl)pyrrole was recovered, (b.p. 88°–100° C. at 19 mm Hg).

Step B: Preparation of (2-pyrryl)methyltrimethylammonium iodide

To a cold solution of 67 g (0.47 mole) of methyliodide in 150 ml of anhydrous ether was added slowly a dry ether solution of 50 gm of 2-(N,N-dimethylaminomethyl)pyrrole (0.37 mole). A white solid begain to precipitate out of solution. The mixture was heated to 30° for 1.5 hours, filtered and washed with 2/×30 ml of ether to obtain 59 gm of 2-pyrryl)methyltrimethylammonium iodide which was used in the next step without further purification.

Step C: Preparation of 2-cyanomethylpyrrole

A mixture of 31 gm (116 mmole) of (2-pyrryl)methyltrimethylammonium iodide, 17.1 g (0.35 mole) sodium cyanide and 300 ml of water was heated on a water bath for 2 hours. The mixture was cooled and extracted with 3/×50 ml of ether. The organic layer was pooled and dried over MgSO$_4$, filtered and evaporated under reduced pressure to remove ether. The residue oil was distilled under high vacuum at 105° C. and 0.3 mm Hg to obtain 4.2 gm of 2-cyanomethylpyrrole.

Step D: Preparation of 2-thioacetamidopyrrole

2-Cyanomethylpyrrole (2.7 g, 25 mmole) was dissolved in 25 ml of dry pyridine. The solution was cooled to 0° C. in a medium pressure glass tube. Hydrogen sulfide was bubbled into the solution for 10 minutes followed by the addition of 1.5 equivalents of triethylamine (5.4 ml). The tube was sealed and heated in a steam bath for 5 hours. After cooling, the tube was opened, venting the excess hydrogen sulfide gas, and the excess pyridine was removed under reduced pressure. Recrystallization from ethyl acetate/hexane yielded 2.2 gm of 2-thioacetamidopyrrole. m.p. 93°–94° C.

Step E: Preparation of
2-(2-pyrryl)methyl-4-(4-pyridyl)thiazole

To a mixture of 2 gm (14.3 mmole) of 2-thioacetamidopyrrole in 30 ml of 95% ethanol was added 1.25 equivalent of α-bromo-4-acetylpyridine hydrobromide (5 gm, 17.8 mmole). The suspension was heated for 1 hour with stirring on a steam bath. The ethanol was removed under reduced pressure and the crude product was triturated in water. The mixture was then made basic with NaOH (pH=12) and resultant solution was extracted with 3×25 ml of methylene chloride, dried over MgSO4, filtered and excess solvent evaporated. The residue was chromatographed (100% ethyl acetate on silica gel) and 0.42 gm of 2-(2-pyrryl)methyl-4-(4-pyridyl)thiazole as an intensely fluorescent red-orange product was isolated. The NMR shows that the molecule has two distinct rotomeric forms in solution at 25° C. The melting point is very broad (164°–180° C.).

EXAMPLE 7

2-(N-Methylimidazolyl)methyl-4-(4-pyridyl)thiazole

Step A: Preparation of
N-methyl-2-hydroxymethylimidazole hydrochloride

1-Methylimidazole (121 mmole, 10 gm) was dissolved in 35 ml of 38% aqueous formaldehyde, decanted into a glass medium pressure tube and the tube sealed. The glass pressure tube was heated to 130° C. for 14 hours. The reaction mixture was cooled and added to 75 ml ethanol containing 18 ml concentrated hydrochloric acid. The mixture was stirred for 10 minutes and then evaporated under reduced pressure. The residue was dissolved in 50 ml of ethanol followed by removing the solvent under reduced pressure. This procedure was repeated twice more. The crude product was recrystallized from ethanol-ether to give 10.8 gm (60% yield) of N-methyl-2-hydroxymethylimidazole, m.p. 158°–160° C.

Step B: Preparation of
N-methyl-2-chloromethylimidazole

N-methyl-2-hydroxymethylimidazole (94 mmole, 10.6 gm) was added portionwise to 22 gm of thionyl chloride (184 mmole), stirring at 0° C. The mixture was then heated to reflux for 1 hour. The excess thionyl chloride was removed under reduced pressure and the crude product was recrystallized from hot methanol to afford 12.3 gm of N-methyl-2-chloromethylimidazole, m.p. 166°–168° C.

Step C: Preparation of
N-methyl-2-cyanomethylimidazole

N-methyl-2-chloromethylimidazole (11.7 g, 71 mmole) was added portionwise to a solution of 8 gm (163 mmole) of pulverized sodium cyanide in 100 ml of dry dimethylsulfoxide while maintaining the reaction mixture temperature between 40°–45° C. After stirring at 45° for 1 hour, the reaction mixture was poured into 200 ml of cold water followed by extraction with 3×200 ml of methylene chloride. The methylene chloride layers were pooled and washed with 2×200 ml 10% cold brine. The methylene chloride layer was then dried over magnesium sulfate (anhydrous), filtered and the solvent removed under reduced pressure to give 2.1 gm of crude product. The crude product was chromatographed through a bed of silica gel (95/5 chloroform:methanol), to afford pure N-methyl-2-cyanomethylimidazole (m.p., picrate, 163°–165° C.

Step D: Preparation of
N-methyl-2-thioacetamidoimidazole

Hydrogen sulfide was bubbled to a solution of 1.4 gm (11.5 mmole) of N-methyl-2-cyanomethylimidazole and 10 ml dry pyridine stirred in a medium pressure glass Carius tube at 0° C. Then 1.5 equivalents of triethylamine was added (2.50 ml) and the pressure tube was sealed and heated on a steam bath for 4 hours. It was cooled and cracked open to vent any excess hydrogen sulfide. The product crystallized out of the solution when it was cooled to 0° C. The crystals were filtered and washed with 2×5 ml of hexane to afford 1.29 gm of N-methyl-2-thioacetamidioimidazole, m.p. 155°–160° C. (decomposition).

Step E: Preparation of
2-(N-methylimidazolyl)methyl-4-(4-pyridyl)thiazole

N-methyl-2-thioacetamidoimidazole (500 mg, 3.5 mmole) was added to 10 ml ethanol. α-Bromo-4-acetylpyridine hydrobromide (1.32 g, 4.38 mmole) was added and the resultant mixture heated for 1 hour on the steam bath. The alcoholic solution was cooled and a precipitate formed which was collected (0.92 g) by filtration. This was dissolved in 5 ml of water, basified to pH 12 with sodium hydroxide and then extracted with 3×20 ml methylene chloride. The pooled methylene chloride layers were dried over magnesium sulfate, filtered and evaporated under reduced pressure. The residue was dissolved in 50 ml of absolute ethanol, bubbled with dry HCl gas to form hydrochloride salt of the product which precipitated upon diluting the ethanol solution with ether. The precipitate was dissolved in hot absolute ethanol/ether and crystallized upon cooling to give 0.35 g of 2-(N-methylimidazolylmethyl)-4-(4-pyridyl)-thiazole dihydrochloride, m.p. 300° C.

EXAMPLE 8

2-(2-Imidazolyl)methyl-4-(4-pyridyl)thiazole

Step A: Preparation of
N-benzyl-2-hydroxymethylimidazole hydrochloride

N-benzylimidazole (20 g, 126 mmole) was placed in a medium pressure glass tube containing 34 ml of 38% formaldehyde. The tube was sealed and heated at 140° C. for 6 hours. After cooling the resultant syrup was decanted and triturated with 75 ml ethanol. 18 ml of concentrated hydrochloric acid was added, followed by evaporation under reduced pressure. The residue was taken up with 100 ml of absolute ethanol and the mixture triturated with ether. After cooling the mixture in ice, the resultant precipitate (23.5 g) was collected. A second crop of 2.5 gms was obtained upon further concentration. The crude product was recrystallized from ethanol-ether to afford 19.8 gm of pure N-benzyl-2-hydroxymethylimidazole hydrochloride, m.p. 158°–160° C.

Step B: Preparation of N-benzyl-2-chloromethylimidazole

A mixture of 10 gm (45 mmole) of N-benzyl-2-hydroxymethylimidazole and 11 gm (92 mmoles) of thionyl chloride was stirred at room temperature for 30 minutes before it was heated to reflux for 30 minutes. The excess thionyl chloride was removed under reduced pressure. The resultant residue (10 gm crude) was crystallized from ethanol/ether to obtain 8.7 gm of N-benzyl-2-chloromethylimidazole, m.p. 180°–182° C.

Step C: Preparation of N-benzyl-2-cyanomethylimidazole

Dry, powdered sodium cyanide (14 gm, 280 mmoles) was added to 80 ml of dry dimethylsulfoxide with stirring at 23° C. Then 1-benzyl-2-chloromethylimidazole hydrochloride (14 gm, 63 mmole) was added portionwise over 10 minutes while maintaining the temperature below 40° C. After the addition was complete, the mixture was stirred at 40° C. for an additional hour. It was diluted with 250 ml methylene chloride and the resulting solution was washed with 4×200 ml of water, dried over MgSO$_4$ and the solvent removed in vacuo. The residue was collected by filtration, dissolved in warm methanol and precipitated with ether to obtain needle-like crystals (8.7 g) of N-benzyl-2-cyanomethylimidazole. m.p. 102.5°–104° C.

Step D: Preparation of 2-cyanomethylimidazole

To a solution of 100 ml dry liquid ammonia in a 250 ml 3-neck round-bottomed flask was added 8.85 gm (45 mmole) of 1-benzyl-2-cyanomethylimidazole. Then, 2.6 gm (113 mmole) of sodium metal was added portionwise until the blue color persisted. The reaction mixture was stirred for an additional 20 minutes before 6.05 gm of ammonium chloride was added portionwise. After the ammonia was evaporated, the crude residue was extracted with hot ethanol, and concentrated under reduced pressure. Recrystallization of the crude product from hot water afforded 4.05 gm of 2-cyanomethylimidazole, m.p. 164°–166° C.

Step E: Preparation of 2-thioacetamidoimidazole

2-Cyanomethylimidazole (0.83 g, 7.7 mmole) in 20 ml of dry pyridine was added to a medium pressure glass tube and was bubbled with hydrogen sulfide gas for 10 minutes. Then 1.5 equivalents of triethylamine (1.1 ml) was added. The tube was sealed and heated in a steam bath for 4 hours. The pressure tube was cooled and the excess hydrogen sulfide vented. Pyridine was removed under reduced pressure. Recrystallization from ethyl acetate-hexane afforded 0.42 gm of 2-thioacetamidoimidazole. m.p. 174° C. (decomposition).

Step F: Preparation of 2-(2-imidazolyl)methyl-4-(4-pyridyl)thiazole

A solution of 0.40 gm (2.8 mmole) 2-thioacetamidoimidazole and 1.25 equivalents of α-bromo-4-acetyl-pyridine hydrobromide in 10 ml of ethanol was heated on the steam bath for 30 minutes. Upon cooling the reaction mixture, a precipitate formed and it was collected by filtration. The precipitate was then dissolved in 15 ml of water and the solution was basified with sodium hydroxide to pH 12, which caused the product to precipitate out of the solution. It was filtered, washed with 2×3 ml ice water, and recrystallized from 25 ml hot water to afford 480 mg of 2-(2-imidazolyl)methyl-4-(4-pyridyl)thiazole as needle-like crystals. m.p. 178°–180° C.

EXAMPLE 9

4-Benzyl-2-(4-pyridyl)thiazole hydrochloride

Crude 1-chloro-3-phenyl-2-propanone (1.73 g, 9.4 mmol) was dissolved in 75 ml ethanol and thioisonicotinamide (3.45 g, 25 mmol) was added. The mixture was warmed to reflux for 1 hour, then tetra-n-butylammonium iodide (200 mg, 0.42 mmol) was added and reflux was continued for 14 hours. Prior to the last 1 hour of reflux, 50 ml of ethanol was distilled from the reaction. Water (25 ml) and 2.5N aqueous sodium hydroxide (25 ml) were added to the cooled reaction, which was then extracted with 2×50 ml of ether. The combined organic extracts were washed with 50 ml of saturated aqueous sodium chloride, dried (sodium sulfate), decanted, and evaporated. The residue was purified by flash column chromatography on silica gel (50 g) eluted with 15% ethyl acetate in dichloromethane, yielding 4-benzyl-2-(4'-pyridyl)thiazole (0.83 g, 35% yield) as a yellow oil which did not crystallize.

The free base was dissolved in methanol (15 ml) and 2.0N aqueous hydrochloric acid (1.7 ml) was added. The solution was evaporated and the dried residue was recrystallized twice from 5 ml of boiling ethanol cooled to 25° C., giving 4-benzyl-2-(4'-pyridyl)thiazole hydrochloride (581 mg) as bright yellow flakes, m.p. 195°–197° C.

EXAMPLE 10

5-Benzyl-2-(4'-pyridyl)thiazole

Isonicotinoyl chloride hydrochloride (1.44 g, 8.09 mmol) was stirred in dry dichloromethane (20 ml) and triethylamine (4.0 ml, 2.9 g, 20 mmol) was added. The mixture was stirred at 25° C. for 5–10 minutes, then cooled in an ice bath. 1-Amino-3-phenyl-2-propanone hydrochloride (1.00 g, 5.39 mmol) was added in portions over 4 minutes. The reaction was stirred 0.5 hour while warming to 25° C., then 0.5 hour at 25° C. Water (5–10 ml) was added and the mixture was stirred 5 minutes before being extracted with ethyl acetate (75 ml). The organic layer was washed with saturated aqueous sodium bicabonate (2×35 ml) and saturated aqueous sodium chloride (35 ml), dried (sodium sulfate), decanted, and evaporated. The residue was purified by flash column chromatography on silica gel (50 g) eluted with 5% isopropanol in dichloromethane, yielding N-(3-phenyl-2-oxopropyl)isonicotinamide (1.23 g, 89% yield) as an orange oil which crystallized (m.p. 85°–86° C.) upon standing. Recrystallization of a portion of this material from toluene raised the m.p. to 86°–88° C.

The amide (600 mg, 2.36 mmol) and 2.01 g (4.97 mmol) of Lawesson's reagent [2,4-bis(4-methoxyphenyl)-1,3-dithia-2,4-diphosphetane-2,4-disulfide] were heated in refluxing toluene (12.0 ml) for 4 hours. The reaction was allowed to cool to 25° C., then 10% aqueous sodium hydroxide (25 ml) was added and the mixture was stirred 2.5 hours. The toluene layer was separated and the aqueous layer was extracted with ether (50 ml). The combined organic layers were washed with 10% aqueous sodium hydroxide (20 ml) and saturated aqueous sodium chloride (20 ml), dried (sodium sulfate), decanted, and evaporated to give 590 mg of amber oil. This residue was purified by flash column chromatography on silica gel (14 g) eluted with 2.5% isopropanol in dichloromethane, yield 5-benzyl-2-

(4'-pyridyl)thiazole as a yellow oil (452 mg, 76% yield) which crystallized upon being seeded. Recrystallization of 483 mg of the product from hexane/toluene cooled slowly from 45°–50° C. to 0° C. gave 254 mg (53% recovery) of colorless needles, m.p. 49°–50° C.

What is claimed is:

1. A compound of formula

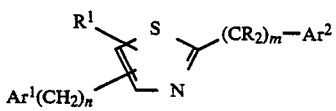 (I)

or a pharmaceutical salt thereof wherein
one of $Ar^1$ and $Ar^2$ is
(a) phenyl of formula

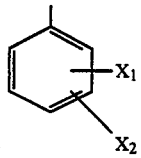

and the other is
(b) 5-(4-pyridyl) of formula

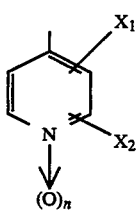

(wherein $X_1$ and $X_2$ independently are
(1) hydrogen;
(2) halo;
(3) —$OR_a$ where $R_a$ represents H or $C_{1-6}$ alkyl;
(4) $C_{1-6}$ alkylthio;
(5) $C_{1-6}$ alkyl;
(6) —$CF_3$;
(7) phenyl;
(8) —CN;
(9) —$NR_aCOR_b$ wherein $R_b$ is H or $C_{1-6}$ alkyl;
(10) —$NO_2$;
(11) —$NR_aR_b$;
(12) —$CONR_aR_b$;
R is hydrogen;
$R^1$ is $R_a$; and
m and n independently are 0 or 1.

2. The compound of claim 1 wherein
$Ar^1$ is 5-(4-pyridyl);
$Ar^2$ is phenyl or 5-(4-pyridyl)
wherein
$X_1$ and $X_2$ independently are
(1) hydrogen;
(2) $C_{1-6}$ alkyl;
(3) —$NR_aR_b$;
R is hydrogen or F;
$R^1$ is H;
n is 0; and
m is 1.

3. A compound of claim 1 which is 2-benzyl-5-(4-pyridyl)thiazole.

4. A pharmaceutical composition for the prevention, control or treatment of autoimmune and chronic inflammatory diseases comprising a pharmaceutical carrier and therapeutically effective amount therefore of a compound of formula (I)

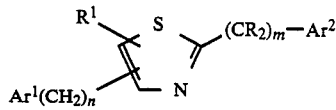 (I)

or a pharmaceutical salt thereof wherein
one of $Ar^1$ and $Ar^2$ is
(a) phenyl of formula

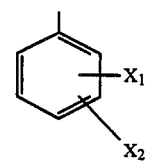

and the other is
(b) 5-(4-pyridyl) of formula

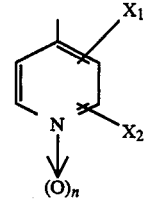

wherein
$X_1$ and $X_2$ independently are
(1) hydrogen;
(2) halo;
(3) —$OR_a$ where $R_a$ represents H or $C_{1-6}$ alkyl;
(4) $C_{1-6}$ alkylthio;
(5) $C_{1-6}$ alkyl;
(6) —$CF_3$;
(7) phenyl;
(8) —CN;
(9) —$NR_aCOR_b$ wherein $R_b$ is H or $C_{1-6}$ alkyl;
(10) —$NO_2$;
(11) —$NR_aR_b$;
(12) —$CONR_aR_b$;
R is hydrogen;
$R^1$ is $R_a$; and
m and n independently are 0 or 1.

5. The composition of claim 4 wherein
$Ar^1$ is 5-(4-pyridyl)
$Ar^2$ is phenyl or 5-(4-pyridyl)
wherein $X_1$ and $X_2$ independently are
(1) hydrogen;
(2) $C_{1-6}$ alkyl;
(3) —$NR_aR_b$;
R is hydrogen or F;
$R^1$ is H;
n is 0; and
m is 1.

6. The composition of claim 4 wherein the active compound is 2-benzyl-5-(4-pyridyl)thiazole.

7. A method for the prevention, control or treatment of autoimmune and chronic antiinflammatory diseases comprising the administration to a mammalian species in need of such treatment an effective amount therefore of a compound of formula (I)

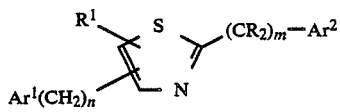 (I)

or a pharmaceutical salt thereof wherein one of $Ar^1$ and $Ar^2$ is (a) phenyl of formula

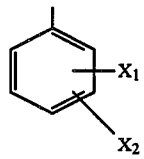

and the other is (b) 5-(4-pyridyl) of formula

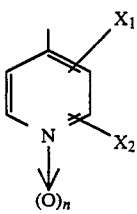

wherein
$X_1$ and $X_2$ independently are
  (1) hydrogen;
  (2) halo;
  (3) $-OR_a$ where $R_a$ represents H or $C_{1-6}$ alkyl;
  (4) $C_{1-6}$ alkylthio;
  (5) $C_{1-6}$ alkyl;
  (6) $-CF_3$;
  (7) phenyl;
  (8) $-CN$;
  (9) $-NR_aCOR_b$ wherein $R_b$ is H or $C_{1-6}$ alkyl;
  (10) $-NO_2$;
  (11) $-NR_aR_b$;
  (12) $-CONR_aR_b$;
R is hydrogen;
$R^1$ is $R_a$; and
m and n independently are 0 or 1.

8. The method of claim 7 wherein
  $Ar^1$ is 5-(4-pyridyl);
  $Ar^2$ is phenyl
    or 5-(4-pyridyl)
    wherein $X_1$ and $X_2$ independently are
    (1) hydrogen;
    (2) $C_{1-6}$ alkyl;
    (3) $-NR_aR_b$;
  R is hydrogen or F;
  $R^1$ is H;
  n is 0; and
  m is 1.

9. The composition of claim 7 wherein the active compound is 2-benzyl-5-(4-pyridyl)thiazole.

* * * * *